(12) United States Patent
Woodward et al.

(10) Patent No.: US 7,273,883 B2
(45) Date of Patent: Sep. 25, 2007

(54) PROSTAGLANDIN EP4 ANTAGONIST

(75) Inventors: David Woodward, Lake Forest, CA (US); Achim H. Krauss, San Marcos, CA (US); Yariv Donde, Dana Point, CA (US); Robert M. Burk, Laguna Niguel, CA (US)

(73) Assignee: Allergan, Inc., Irvine, CA (US)

( * ) Notice: Subject to any disclaimer, the term of this patent is extended or adjusted under 35 U.S.C. 154(b) by 334 days.

(21) Appl. No.: 10/952,418

(22) Filed: Sep. 27, 2004

(65) Prior Publication Data

US 2005/0065200 A1 Mar. 24, 2005

Related U.S. Application Data

(63) Continuation-in-part of application No. 10/780,441, filed on Feb. 12, 2004, now Pat. No. 7,217,725, which is a continuation-in-part of application No. 10/300,492, filed on Nov. 19, 2002, now Pat. No. 6,716,864, which is a continuation of application No. 10/071,449, filed on Feb. 8, 2002, now Pat. No. 6,511,999, which is a continuation-in-part of application No. 09/840,675, filed on Apr. 23, 2001, now Pat. No. 6,369,089, which is a continuation of application No. 09/677,372, filed on Sep. 14, 2000, now abandoned.

(51) Int. Cl.
*A61K 31/422* (2006.01)
(52) U.S. Cl. ...................................... 514/374
(58) Field of Classification Search ................ 514/374
See application file for complete search history.

(56) References Cited

U.S. PATENT DOCUMENTS

| | | | |
|---|---|---|---|
| 4,808,608 | A | 2/1989 | Guindon et al. |
| 5,491,254 | A | 2/1996 | Sato et al. |
| 6,369,082 | B1 | 4/2002 | Lacombe et al. |
| 6,369,089 | B1 | 4/2002 | Burk et al. |
| 6,407,250 | B1 | 6/2002 | Burk et al. |
| 6,410,583 | B1 | 6/2002 | Labelle et al. |
| 2001/0051624 | A1 | 12/2001 | Jones |
| 2003/0055077 | A1 | 3/2003 | Jones |
| 2003/0158246 | A1 | 8/2003 | Berthelette et al. |

FOREIGN PATENT DOCUMENTS

| | | |
|---|---|---|
| EP | 837 052 A1 | 4/1998 |
| WO | WO 98/25919 | 6/1998 |
| WO | WO 99/62555 | 12/1999 |

OTHER PUBLICATIONS

Golub et al., Science, vol. 286, Oct. 15, 1999, pp. 531-537.*
Ney, P., et al., *PGD$_2$ and its mimetic ZK 110.841 are potent inhibitors of receptor-mediated activation of human neutrophils*, Eicosanoids (1991) 4:21-28.

Wright, D.H., et al., "*Characterization of the recombinant human prostanoid DP receptor and identification of L-644,698, a novel selective DP agonist*" British Journal of Pharmacology (1998) 123, 1317-1324.

Boie, Y, et al., "Molecular cloning and characterization of the human prostanoid DP receptor" *Journal of Biological Chemistry*, vol. 270, No. 32, Aug. 11, 1995, pp. 18910-18916.

Breyer, M.D., et al., "Functional and molecular aspects of renal prostaglandin receptors" *J. Am. Soc.Nephrol*, 1996;7;8-17.

Coleman, R.A., "Prostanoid Receptors" *Eicosanoids From Biotechnology to Therapeutic Applications*, Plenum Press, 1996, Chp. 14, 137-154.

Darius, H., et al., Inhibition of human platelets and polymorphonuclear neutrophils by the otent and metabolically stable prostaglandin D2 analog ZK 118.182 *European Journal of Pharm*, 258(1994) 207-213.

Giles, H., et al., The classification of prostaglandin DP-receptors in platelets and vasculature using BW A868C, a novel selective and potent competitive antagonist, *Br. J. Pharmacol.*, (1989), 96, 291-300.

(Continued)

*Primary Examiner*—Laura L. Stockton
(74) *Attorney, Agent, or Firm*—Brent A. Johnson; Martin A. Voet

(57) ABSTRACT

Disclosed herein are methods and compositions related to compound 1

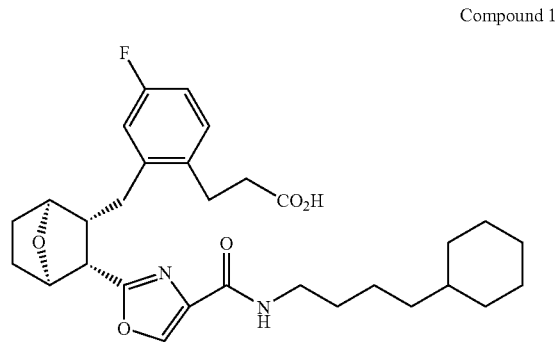

Compound 1 or a pharmaceutically acceptable salt, or a prodrug thereof (all of which are referred to hereafter, collectively or individually, as "compound 1"), which is an antagonist of a prostaglandin $EP_4$ receptor, or is a prostaglandin $EP_4$ antagonist.

Also disclosed is a method comprising administering a prostaglandin $EP_4$ antagonist to a mammal suffering from, or at risk of developing, a disease or condition selected from the group consisting of cancer, immunological disorders, neurodegenerative disorders, ocular diseases, hepatic diseases, renal diseases, septicemia, fibromyalgia, dermatological disorders, and antipyrexia.

4 Claims, 5 Drawing Sheets

OTHER PUBLICATIONS

Hirai, H, et al., "Prostaglandin D2 selectively induces chemotaxis in T helper type 2 cells, eosinophils, and basophils via seven-transmembrane receptor CRTH2", *J. Exp. Med, The Rockfeller Univ. Press*, vol. 192, No. 2, Jan. 15, 2001, 255-261.

Ichikawa, A.,"Molecular aspects of the structures and functions of the prostaglandin E receptors", *J of Lipid Mediators and Cell Signalling*, 14 (1996) 83-87.

Matsuoka, T., et al., "Prostaglandin D2 as a Mediator of allergic asthma", *Science* vol. 287, Mar. 17, 2000, pp. 2013-2017.

Negishi, M. et al., "Prostanoid receptors and their biological actions" *Prog. Lipid Res.* vol. 32, No. 4, pp. 417-434, 1993.

Pons, F., et al., "Pro-inflammatory and anti-inflammatory effects of the stable prostaglandin D2 analogue ZK.182" *European Journal of Pharm*, 261 (1994) 237-247.

Rangachari, P.K., et al., "Effects of a selective DP receptor agonist (BW 245C) and antagonists (BW A868C) on the canine colonic epithelium : an argument for a different DP receptor", *The Journal of Pharmacology and experimental therapeutics*, vol. 275, No. 2, 611-617 (1995).

Tsuri, T., et al, "Bicyclo [2.2.1]heptane and 6,6-dimethylbicyclo[3.1.1]heptane Derivatives: orally active, potent and selective prostaglandin D2 receptor antagonists" *J. Med. Chem*, 1997, 40, 3504-3507.

Wright, D.H., et al., "A novel biological role for prostaglandin D2 is suggested by distribution studies of the rat DP prostanoid receptor", *European Journal of Pharmacology*, 377 (1999) 101-115.

\* cited by examiner (a) CH$_3$I, DBU, acetone; (b) DIBAL, toluene -78 °C to rt; (c) PDC, MgSO$_4$, 4Å molecular sieves, CH$_2$Cl$_2$ 74% from 1; (d) Ph$_3$PCHCO$_2$CH$_3$, toluene 95%;
(e) (Ph$_3$P)$_3$RhCl, H$_2$, EtOH 80%; (f) DIBAL, toluene -78 °C to rt 99%;
(g) Dimethylthexylsilyl chloride, DMAP, Et$_3$N, CH$_2$Cl$_2$ 83%.

(a) Mg, THF, 65 °C; (b) EtMgBr, 0 °C to rt 69%; (c) Ac$_2$O, pyridine 77%; (d) (Im)$_2$S, ClCH$_2$CH$_2$Cl, 60 °C 94%; (e) n-Bu$_3$SnH, AIBN, toluene, 110 °C 84%; (f) CrO$_3$, H$_2$SO, acetone; (g) MeOH, AcCl 88% for 2 steps; (h) CrO$_3$, H$_2$SO$_4$, acetone.

(a) L-serine benzyl ester hydrochloride, DCC, HOBt, Et$_3$N, THF 80% for 2 steps;
(b) PPh$_3$, CCl$_4$, i-Pr$_2$NEt, CH$_3$CN 69%; (c) BrCCl$_3$, DBU, CH$_2$Cl$_2$ 0 °C 75%; (d) H$_2$, Pd(OH)$_2$/C, EtOAc 100%; (e) i. (COCl)$_2$, cat. DMF, CH$_2$Cl$_2$; ii. 4-cyclohexylbutylammonium chloride, Et$_3$N, CH$_2$Cl$_2$ 78%; (f) NaOH, aqueous THF, 95%.

PROSTAGLANDIN EP4 ANTAGONIST

CROSS-REFERENCE TO RELATED APPLICATIONS

This application is a continuation-in-part of U.S. patent application Ser. No. 10/780,441, filed on Feb. 12, 2004 now U.S. Pat. No. 7,217,725, which is a continuation-in-part of U.S. patent application Ser. No. 10/300,492, now U.S. Pat. No. 6,716,864, filed on Nov. 19, 2002; which is a continuation of U.S. patent application Ser. No. 10/071,449, now U.S. Pat. No. 6,511,999, filed on Feb. 8, 2002; which is a continuation-in-part of U.S. patent application Ser. No. 09/840,675, now U.S. Pat. No. 6,369,089 filed on Apr. 23, 2001; which is a continuation of U.S. patent application Ser. No. 09/677,372 filed Sep. 14, 2000, now abandoned. All of the aforementioned patent applications are incorporated by reference herein.

Said U.S. Pat. No. 6,369,089 filed on Apr. 23, 2001; which is a continuation of U.S. patent application Ser. No. 09/677,372 filed Sep. 14, 2000, now abandoned, is also related to U.S. application Ser. No. 09/661,771, also filed Sep. 14, 2000, now U.S. Pat. No. 6,407,250 which was incorporated by reference therein.

Thus, the present application claims priority to the disclosure of all of the foregoing patent applications, and the effective filing dates of the material in any of said applications is identical to the effective filing date of said material in the present application.

BACKGROUND OF THE INVENTION

1. Field of the Invention

This disclosure relates to pharmaceutical compositions and medical treatments. In particular, this disclosure relates to the use of prostaglandin $EP_4$ antagonists in said compositions and treatments.

2. Description of the Related Art

Prostaglandin $EP_4$ antagonists are believed in the art to have a number of useful medicinal properties. WO0149661 discloses compounds which "strongly bind to $PGE_2$ receptors (in particular, subtype $EP_4$), so that the [compounds] are expected to be useful in the prevention and/or treatment of immunopathy, asthma, bone dysplasia, nerve cellular death, lung failure, hepatopathy, acute hepatitis, nephritis, renal failure, hypertension, myocardial ischemia, systemic inflammatory reaction syndrome, septicemia, hemophagocytosis syndrome, macrophage activation syndrome, Still disease, Kawasaki disease, burn, systemic granuloma, ulcerative colitis, Crohn disease, hypercytokinemia at dialysis, multiple organ failure, shock, sleep disorder, platelet aggregation and so on." WO0149661 also discloses that " compounds which can bind on $EP_4$ subtype receptor strongly are expected to be useful for the prevention and/or treatment of immunological diseases (autoimmune diseases such as amyotrophic lateral sclerosis (ALS), multiple sclerosis, Sjoegren's syndrome, chronic rheumarthrosis and systemic lupus erythematosus etc., and rejection after organ transplantation etc.), asthma, abnormal bone formation, neuronal cell death, lung failure, liver damage, acute hepatitis, nephritis, renal insufficiency, hypertension, myocardiac ischemia, systemic inflammatory response syndrome, sepsis, hemophagous syndrome, macrophage activation syndrome, Still's disease, Kawasaki disease, burn, systemic granulomatosis, ulcerative colitis, Crohn's disease, hypercytokinemia at dialysis, multiple organ failure, and shock etc. Further, it is thought that $EP_4$ subtype receptor relates to sleeping disorder and blood platelet aggregation, so such compounds are expected to be useful for the prevention and/or treatment of these diseases."

WO0015608 discloses "because of binding strongly to PGE2 receptors (in particular, subtype $EP_4$), the compounds [disclosed in the reference] are useful in preventing and/or treating immunologic diseases (autoimmune diseases such as amyotrophic lateral sclerosis (ALS), rejection reactions following organ transplantation, etc.), asthma, bone dysplasia, nerve cell death, lung failure, liver failure, etc. Also, these compounds participate in sleep disorder and platelet agglutination and, therefore, are useful in treating diseases relating thereto." WO0015608 also discloses "compounds of the present invention of formula (I) bind strongly on subtype $EP_4$ and therefore are useful for the prophylaxis and/or treatment of immune diseases (autoimmune diseases (amyotrophic lateral sclerosis (ALS), multiple sclerosis, Sjoegren's syndrome, arthritis, rheumatoid arthritis, systemic lupus erythematosus, etc.), post-transplantation graft rejection, etc.), asthma, abnormal bone formation, neurocyte death, pulmopathy, hepatopathy, acute hepatitis, nephritis, renal insuffiency, hypertension, myocardial ischemia, systemic inflammatory syndrome, pain induced by ambustion, sepsis, hemophagocytosis syndrome, macrophage activation syndrome, Still's diseases, Kawasaki diseases, burn, systemic granuloma, ulcerative colitis, Crohn's diseases, hypercytokinemia at dialysis, multiple organ failure, shock, etc. They are also related with sleeping disorders and platelet coagulations, and therefore they are thought to be applicable to these diseases."

In citing the foregoing references, and other references cited herein, applications make no admission as to whether any of said references constitutes prior art. Rather, the determination of what constitutes prior art is a legal decision made on the basis of the dates said references were made available to the public, the authors or inventors of said references, and the effective filing date of the disclosure made herein.

BRIEF DESCRIPTION OF THE INVENTION

Disclosed herein are methods and compositions related to compound 1

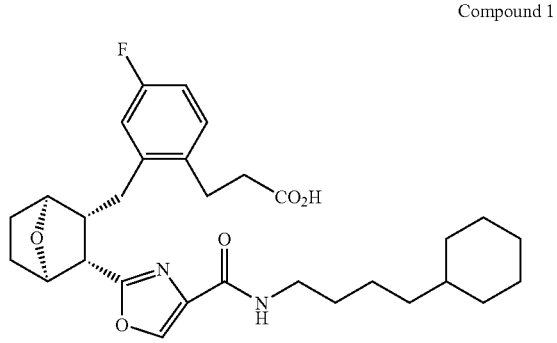

Compound 1 or a pharmaceutically acceptable salt, or a prodrug thereof (all of which are referred to hereafter, collectively or individually, as "compound 1"), which is an antagonist of a prostaglandin $EP_4$ receptor, or is a prostaglandin $EP_4$ antagonist.

Also disclosed is a method comprising administering a prostaglandin $EP_4$ antagonist to a mammal suffering from, or at risk of developing, a disease or condition selected from the group consisting of cancer, immunological disorders, neurodegenerative disorders, ocular diseases, hepatic diseases, renal diseases, septicemia, fibromyalgia, dermatological disorders, and antipyrexia.

BRIEF DESCRIPTION OF THE DRAWING FIGURES

DETAILED DESCRIPTION OF THE INVENTION

Figure 1:
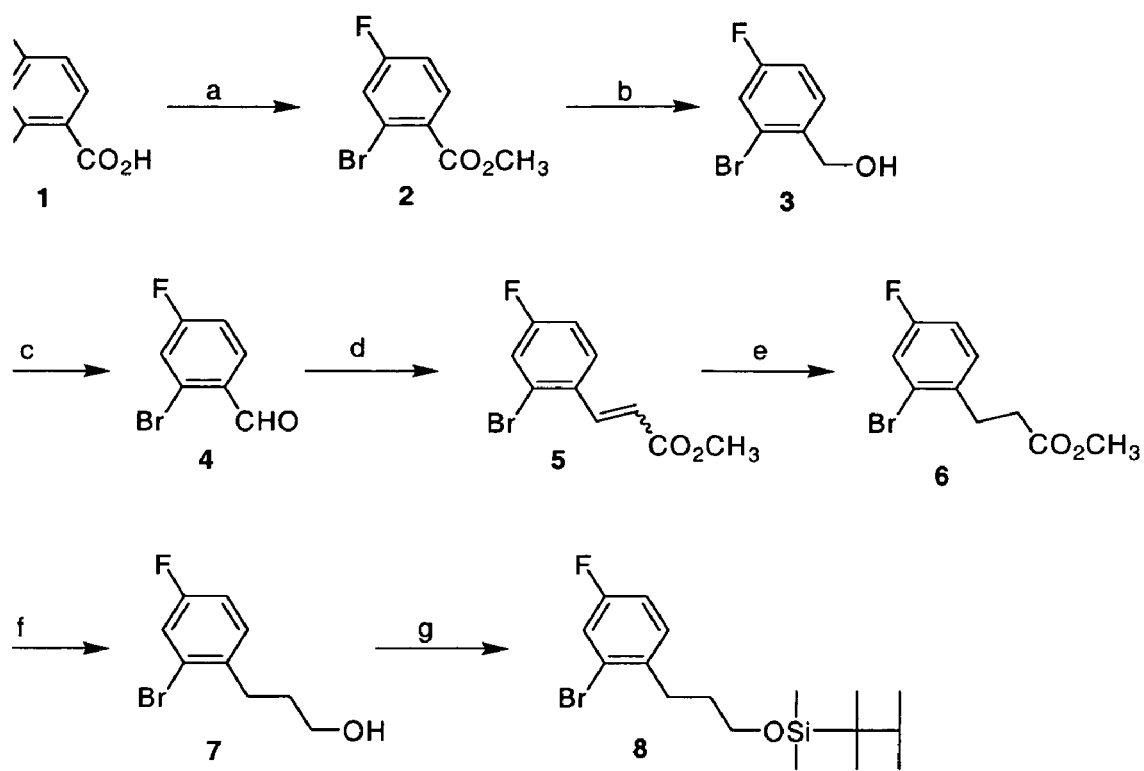
FIGS. 1-3 illustrate one synthetic method for obtaining compound 1.

One embodiment comprises compound 1. Compound 1 is used in a medical sense to treat or prevent a condition or disease which is mediated by a prostaglandin $EP_4$ receptor.

A condition or disease which is mediated by the prostaglandin $EP_4$ receptor is one in which the binding or lack of binding, or the agonism or antagonism of the prostaglandin $EP_4$ receptor, causes or contributes to the cause of a disease or condition, or a symptom thereof.

Compound 1 has several medical uses, including treatment of skeletal disorders, including osteoporosis and bone dysplasia; cancer, including colorectal cancer; immunological disorders, including but not limited to Sjoegren's syndrome, multiple sclerosis, amyotrophic lateral sclerosis, rheumatoid arthritis, and lupus erythematosus; neurodegenerative disorders, including stroke; ocular diseases, including dry eye, neurodegenerative conditions, glaucoma, non-exudative age related macular degeneration, exudative age related macular degeneration, choroidal neovascularization, acute macular neuroretinopathy, cystoid macular edema, diabetic macular edema, Behcet's disease, diabetic retinopathy, retinal arterial occlusive disease, central retinal vein occlusion, uveitic retinal disease, retinal detachment, trauma, conditions caused by laser treatment, conditions caused by photodynamic therapy, photocoagulation, radiation retinopathy, epiretinal membranes, proliferative diabetic retinopathy, branch retinal vein occlusion, anterior ischemic optic neuropathy, non-retinopathy diabetic retinal dysfunction, and retinitis pigmentosa; pulmonary respiratory diseases, including asthma and chronic obstructive pulmonary disorder; hepatic diseases including hepatitis; myocardial ischemia; renal disease, including dialysis adjunct and nephritis; systemic hypertension; septicemia; sleep disorders; shock, including multiple organ failure; fibromyalgia; gastrointestinal disease, including irritable bowel syndrome, diarrhea, ulcerative colitis; Still's disease; Kawasaki's disease; Crohn's disease; inflammatory bowel disease; hemophagocytosis syndrome; dermatological disorders, including dermatitis, psoriasis, and acne; systemic granuloma; burns and scalds; pain, including migraine; and antipyrexia.

In one embodiment compound 1 is used to treat or prevent skeletal disorders including osteoporosis and bone dysplasia.

In another embodiment compound 1 is used to treat or prevent cancer including colorectal cancer.

In another embodiment compound 1 is used to treat or prevent immunological disorders, including but not limited to Sjoegren's syndrome, multiple sclerosis, amyotrophic lateral sclerosis, rheumatoid arthritis, and lupus erythematosus.

In another embodiment compound 1 is used to treat or prevent neurodegenerative disorders, including stroke.

In another embodiment compound 1 is used to treat or prevent ocular diseases including dry eye, and glaucoma.

In another embodiment compound 1 is used for neuroprotection in an ocular disease such as glaucoma, non-exudative age related macular degeneration, exudative age related macular degeneration, choroidal neovascularization, acute macular neuroretinopathy, cystoid macular edema, diabetic macular edema, Behcet's disease, diabetic retinopathy, retinal arterial occlusive disease, central retinal vein occlusion, uveitic retinal disease, retinal detachment, trauma, conditions caused by laser treatment, conditions caused by photodynamic therapy, photocoagulation, radiation retinopathy, epiretinal membranes, proliferative diabetic retinopathy, branch retinal vein occlusion, anterior ischemic optic neuropathy, non-retinopathy diabetic retinal dysfunction, and retinitis pigmentosa.

In another embodiment compound 1 is used to treat or prevent pulmonary respiratory diseases such as asthma and chronic obstructive pulmonary disorder.

In another embodiment compound 1 is used to treat or prevent hepatic diseases including hepatitis.

In another embodiment compound 1 is used to treat or prevent myocardial ischemia.

In another embodiment compound 1 is used to treat or prevent renal disease including use as a dialysis adjunct and the treatment or prevention of nephritis.

In another embodiment compound 1 is used to treat or prevent systemic hypertension.

In another embodiment compound 1 is used to treat or prevent septicemia.

In another embodiment compound 1 is used to treat or prevent sleep disorders.

In another embodiment compound 1 is used to treat or prevent shock including multiple organ failure.

In another embodiment compound 1 is used to treat or prevent fibromyalgia

In another embodiment compound 1 is used to treat or prevent gastrointestinal disease, including irritable bowel syndrome, diarrhea, and ulcerative colitis.

In another embodiment compound 1 is used to treat or prevent Still's disease.

In another embodiment compound 1 is used to treat or prevent Kawasaki's disease.

In another embodiment compound 1 is used to treat or prevent Crohn's disease.

In another embodiment compound 1 is used to treat or prevent hemophagocytosis syndrome.

In another embodiment compound 1 is used to treat or prevent dermatological disorders including dermatitis, psoriasis, and acne.

In another embodiment compound 1 is used to treat or prevent systemic granuloma

In another embodiment compound 1 is used to treat burns and scalds

In another embodiment compound 1 is used to treat or prevent pain.

In another embodiment compound 1 is used to treat or prevent antipyrexia.

Compositions, formulations, dosage forms, medicaments, kits, and pharmaceutical products comprising compound 1 for the medical uses described herein are also contemplated.

A "pharmaceutically acceptable salt" is any salt that retains the activity of the parent compound and does not impart any additional deleterious or untoward effects on the subject to which it is administered and in the context in which it is administered compared to the parent compound.

Pharmaceutically acceptable salts of acidic functional groups may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted.

Those skilled in the art will readily understand that for administration the compounds disclosed herein can be admixed with pharmaceutically acceptable excipients which, per se, are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgement of the prescribing physician. The therapeutically effective dosage of the presently useful compound or compounds is preferably in the range of about 0.5 ng/kg/day or about 1 ng/kg/day to about 100 mg/kg/day.

For ophthalmic application, solutions are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

The actual dose of the active compounds of the present invention depends on the specific compound, and on the condition to be treated; the selection of the appropriate dose is well within the knowledge of the skilled artisan.

Figure 2:
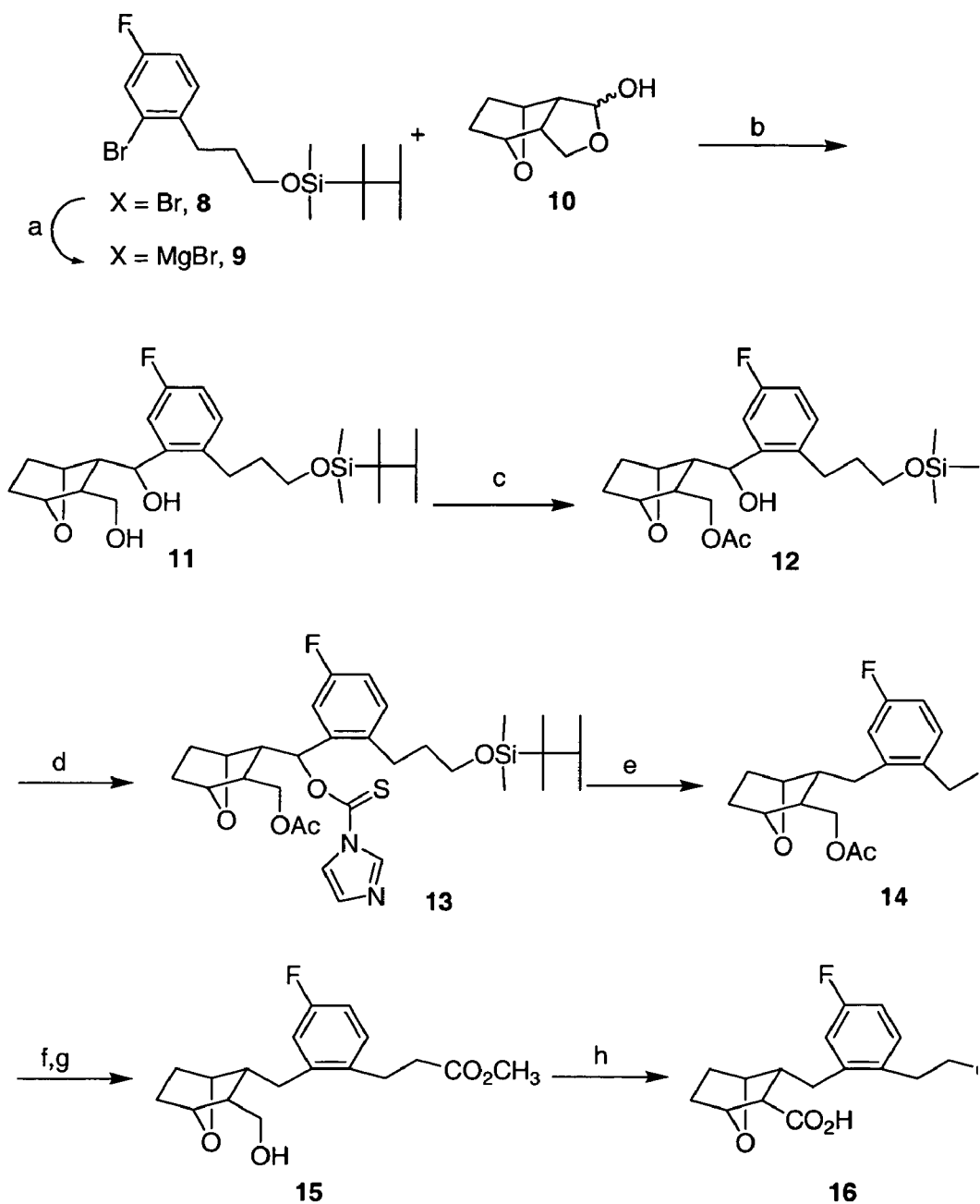
Figure 3:
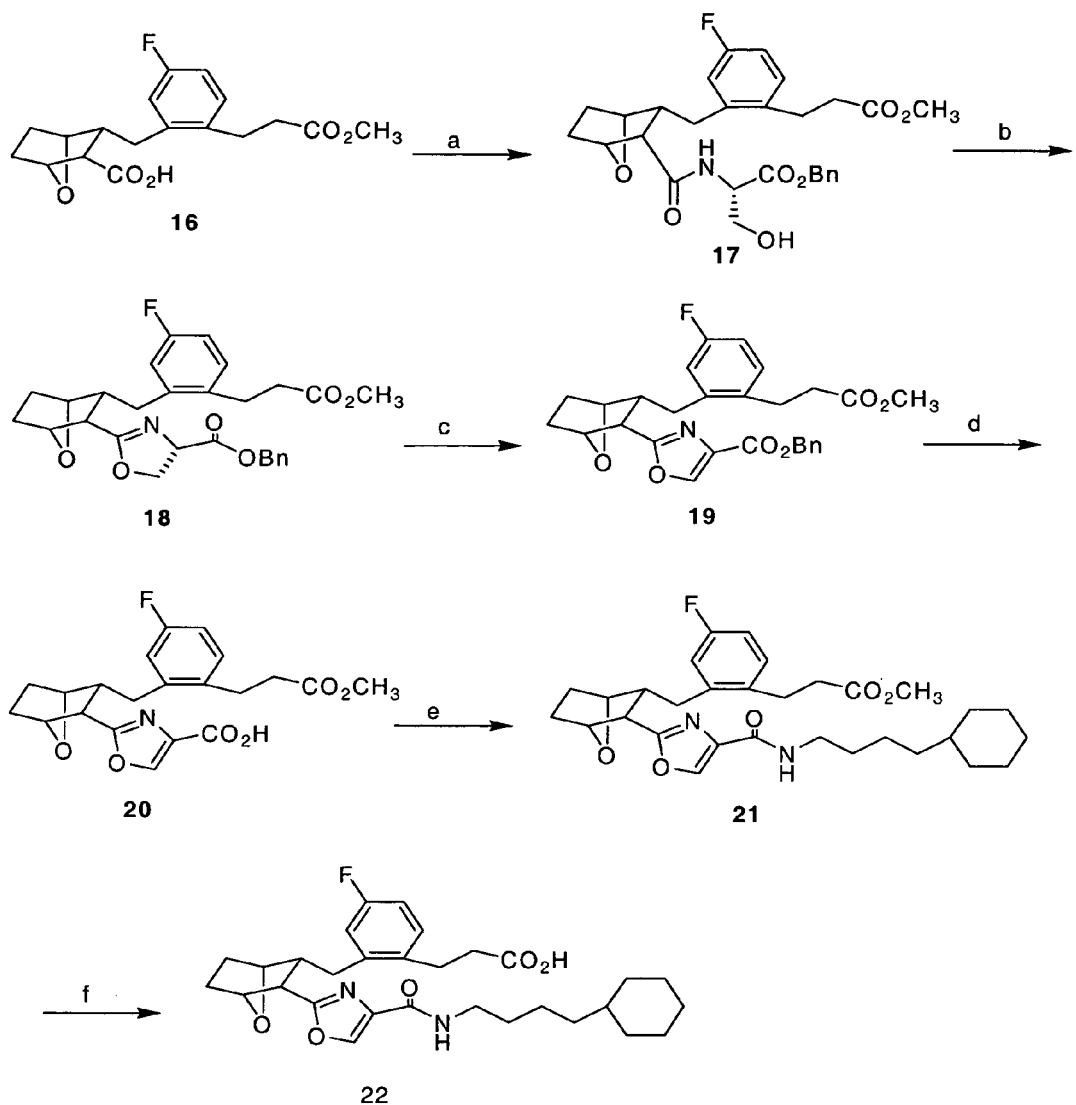

The following Examples 1-22 describe a method of synthesizing the compound shown herein to be a prostaglandin $EP_4$ antagonist, wherein the numbering of the Examples corresponds to the numbering of the various intermediates and final compounds shown in FIGS. 1 through 3.

EXAMPLE 1

2-Bromo-4-fluorobenzoic acid. The named compound is purchased from Marshallton Research Laboratories Inc., P.O. Box 930, King, N.C. 27021.

EXAMPLE 2

2-Bromo-4-fluorobenzoic acid, methylester. A solution of 2-bromo-4-fluorobenzoic acid (5 g, 22.8 mmol), DBU (5.21 g, 34.2 mmol), and methyl iodide (6.48 g, 45.7 mmol) in acetone (23 mL) was stirred at room temperature for 2 h. The reaction was concentrated in vacuo and the residue partitioned between EtOAc and 1 M HCl. The organic portion was washed with saturated aqueous $NaHCO_3$, brine and then was dried ($MgSO_4$), filtered and evaporated to give the ester of Example 2 (5.18 g) which was used directly in the next step.

EXAMPLE 3

(2-Bromo-4-fluorophenyl) methanol. DIBAL-H (56 mL, 56 mmol, 1M/toluene) was added to a solution of the ester of Example 2 (5.18 g, 22.2 mmol) in toluene (50 mL) at −78° C. After 1 h, the reaction was warmed to room temperature and quenched by dropwise addition of 1 M NaOH. The mixture was extracted with EtOAc. The organic portion was washed with brine and then was dried ($MgSO_4$), filtered, and evaporated to give the alcohol of Example 3 (4.55 g) which was used directly in the next step.

EXAMPLE 4

2-Bromo-4-fluorobenzaldehyde. A mixture of the alcohol of Example 3 (4.55 g, 22.2 mmol), PDC (10.0 g, 26.6 mmol), $MgSO_4$ (10.0 g) and crushed 4 Å molecular sieves (10.0 g) in $CH_2Cl_2$ (44 mL) was stirred for 12 h. The mixture was diluted with ether and filtered through celite. The solvent was evaporated and the residue purified by flash column chromatography on silica gel (10% EtOAc/hexanes) to give the aldehyde of Example 4 (3.43 g, 16.9 mmol, 74% from 2-bromo-4-fluorobenzoic acid).

EXAMPLE 5

(E)-3-(2-Bromo-4-fluorophenyl)acrylic acid methyl ester. A mixture of the aldehyde of Example 4 (4.5 g, 22.2 mmol) and methyl(triphenylphosphoranylidene)acetate (8.91 g, 36.6 mmol) in toluene (22 mL) was stirred for 12 h. The solvent was removed in vacuo and the residue was purified by flash chromatography on silica gel (5% EtOAc/hexanes) to give the ester of Example 5 (5.46 g, 21.1 mmol, 95%).

EXAMPLE 6

3-(2-Bromo-4-fluorophenyl)propionic acid methyl ester. A mixture of $(Ph_3P)_3RhCl$ (1.49 g, 1.61 mmol) and the ester of Example 5 (4.17 g, 16.1 mmol) in ethanol (30 mL) was evacuated and purged with $H_{2(g)}$. The mixture was stirred under 1 atm $H_2$ pressure for 12 h. The solvent was removed and the residue was purified by flash column chromatography on silica gel (5% EtOAc/hexanes) to give the ester of Example 6 (3.50 g, 13.4 mmol, 80%).

EXAMPLE 7

3-(2-Bromo-4-fluorophenyl)propan-1-ol. A −78° C. solution of the ester of Example 6 (3.50 g, 13.4 mmol) in toluene (20 mL) was treated dropwise with DIBAL-H (33.5 mL, 33.5 mmol, 1 M/toluene). After 1 h, the reaction was warmed to room temperature and then was quenched with dropwise addition of 1 M $H_2SO_4$. The warm mixture was poured onto ice and extracted with EtOAc. The organic portion was washed with saturated $NaHCO_3$ solution and brine and then was dried ($MgSO_4$), filtered, and evaporated. Purification by flash column chromatography on silica gel (25% EtOAc/hexanes) gave the alcohol of Example 7 (3.09 g, 13.3 mmol, 99%).

EXAMPLE 8

[3-(2-Bromo-4-fluoro-phenyl)-propoxyl]-dimethyl-(1,1,2-trimethyl-propyl)-silane. A solution of the alcohol of Example 7, (2.1 g, 9.0 mmol), dimethylthexylsilyl chloride (2.8 mL, 14.2 mmol, Aldrich), $Et_3N$ (1.36 mL, 9.76 mmol, Aldrich) and 4-(dimethylamino)pyridine (48 mg, 0.39 mmol, Aldrich) in $CH_2Cl_2$ (16 mL, Aldrich) was stirred for 18 h. The solution was poured into saturated aqueous $NaHCO_3$ solution (25 mL) and the mixture extracted with $CH_2Cl_2$ (2×25 mL). The combined $CH_2Cl_2$ solution was dried ($MgSO_4$), filtered, evaporated and purified by flash column chromatography on silica gel (2% EtOAc/hexanes→30%→40%) to give the silane of Example 8 (2.792 g, 7.4 mmol, 83%).

EXAMPLE 9

A mixture of Mg turnings (173 mg, 7.1 mmol, Aldrich), iodine (2 crystals), and 1,2-dibromoethane (20 μL) in dry THF (2.6 mL, Aldrich) was heated in a 64° C. oil bath with magnetic stirring until the iodine color disappeared (ca. 15 min.). The resulting mixture was allowed to cool to room temperature and a solution of the bromide of Example 8 (1.882 g, 5.0 mmol) in 1.5 mL THF was added dropwise by cannula, rinsing with 1 mL THF. The mixture was heated in the 64° C. oil bath for 3 h, allowed to cool to room temperature and used directly in the next step.

EXAMPLE 10

3aR-(3aα, 4α, 7α, 7aα)]-1-Hydroxyhexahydro-4,7-epoxyisobenzofuran. The named compound is prepared according to Das, J.; Haslanger, M. F.; Gougougoutas, J. Z.; Malley, M. F. Synthesis of Optically Active 7-Oxabicyclo[2.2.1]heptanes and Assignment of Absolute Configuration. *Synthesis* 1987, 1100-1103 except in the final dibal reduction of the corresponding lactone, the reaction was quenched with methanol and worked up with aqueous NaOH.

EXAMPLE 11

1-(2-{3-[Dimethyl-(1,1,2-trimethyl-propyl)-silanyloxy]-propyl}-5-fluoro-phenyl)-1-((1R, 2S, 3R, 4R-3-hydroxymethyl-7-oxa-bicyclo[2.2.1]hept-2-yl)-methanol. An ice-cold solution of lactol 10 (3aR-(3aα, 4α, 7α, 7aα)]-1-Hydroxyhexahydro-4,7-epoxyisobenzofuran (708 mg, 4.53 mmol) in 2.4 mL of dry THF (Aldrich) was treated dropwise with EtMgBr (4.5 mL, 4.5 mmol, 1 M/THF, Aldrich). After 20 min., the Grignard solution from Example 9 above was added by cannula and the solution allowed to warm to room temperature.

After 16 h, the reaction was quenched by addition of 2.8 mL of saturated $NH_4Cl$ solution with cooling. The resulting mixture was stirred for 2 h and then $CH_2Cl_2$ (10 mL) was added. The solution was decanted from the gum, the gum washed further with $CH_2Cl_2$ (3×10 mL), and the combined $CH_2Cl_2$ solution was dried ($MgSO_4$), filtered, and evaporated. Purification of the crude product by flash column chromatography on silica gel (40% EtOAc/hexanes) gave the diol of Example 11 (1.386 g, 3.1 mmol, 69%) as an oil.

EXAMPLE 12

Acetic acid (1R, 2R, 3S, 4R)-3-[1-(2-{3-[dimethyl-(1,1,2-trimethyl-propyl)-silanyloxy]-propyl}-5-fluoro-phenyl)-1-hydroxy-methyl]-7-oxa-bicyclo[2.2.1]hept-2-ylmethyl ester. The diol of Example 11 (713 mg, 1.62 mmol) was co-evaporated with benzene (2×2 mL). The residue was taken into 1.5 mL of dry pyridine (Aldrich) and was treated with $Ac_2O$ (195 μL, 2.07 mmol, Aldrich). The solution was allowed to stir for 17 h and then was evaporated and co-evaporated twice with toluene. Flash column chromatography on silica gel (20% EtOAc/hexanes→30%→40%→50%) gave the monoacetate of Example 12 (564 mg, 1.17 mmol, 72%).

EXAMPLE 13

Acetic Acid (1R, 2R, 3R, 4R)-3-[1-(2-{3-[dimethyl-(1,1,2-trimethyl-propyl)-silanyloxy]-propyl}-5-fluoro-phenyl)-1-(1-imadazol-1-yl-methanethioyloxy)-methyl]-7-oxa-bicyclo[2.2.1]hept-2-ylmethyl ester. The acetate of Example 12 (5.64 mg, 1.17 mmol) was co-evaporated with benzene (2×2 mL). The residue was taken into dry dichloroethane (0.8 mL, Aldrich) and thiocarbonyldiimidazole (643 mg, 3.61 mmol, Aldrich) was added. The mixture was heated in a 60° C. oil bath with stirring. After 1 h, there was a considerable amount of starting material and so the solvent level was reduced under a nitrogen stream and the reaction allowed to stir further for another 1 h at which time the reaction was complete (TLC analysis). The mixture was allowed to cool to room temperature and then purified by flash column chromatography on silica gel (30% EtOAc/hexanes→40%) which gave the ester of Example 13 (506 mg, 0.93 mmol, 79%).

EXAMPLE 14

Acetic acid (1R, 2R, 3R, 4R)-3-(2-{3-[dimethyl-(1,1,2-trimethyl-propyl)-silanyloxy]-propyl}-5-fluoro-benzyl)-7-oxa-bicyclo[2.2.1]hept-2-ylmethyl ester. A solution of the ester of Example 13 (506 mg, 0.93 mmol), $Bu_3SnH$ (1.44 mL, 5.35 mmol, Aldrich), and AIBN (53 mg, 0.32 mmol, Alfa) in toluene (45 mL, Aldrich) was heated in a 110° C. oil bath. After 2 h, the reaction was not complete (TLC analysis) and so another 53 mg of AIBN was added. After 1 h of further heating the reaction was complete. The solution was allowed to cool to room temperature, was evaporated and then purified by flash column chromatography on silica gel (100% hexanes→5% EtOAc/hexanes→10%) which gave the ester of Example 14 (366 mg, 0.78 mmol, 84%).

EXAMPLE 15

3-[4-Fluoro-2-((1R, 2R, 3R, 4R)-3-hydroxymethyl-7-oxa-bicyclo[2.2.1]hept-2-ylmethyl)-phenyl]-propionic acid methyl ester. A solution of the ester of Example 14 (577 mg, 1.2 mmol) in acetone (6 mL, B & J brand) was treated dropwise with Jones reagent (0.84 mL, 2.5 M in Cr(VI), 2.1 mmol). After 20 min., the reaction was quenched by addition of isopropyl alcohol (0.5 mL). The mixture was allowed to stir for 15 min. and then was filtered through celite. The filtrate was evaporated and the residue was partitioned between $CH_2Cl_2$ (20 mL) and 3:1 $H_2O$/brine (20 mL). The aqueous portion was further extracted with $CH_2Cl_2$ (2×20 mL) and the combined $CH_2Cl_2$ solution was dried ($MgSO_4$), filtered and evaporated to leave the acid as a slightly yellow oil that was used directly in the next step.

The crude acid was taken into a solution of 1% v/v AcCl/MeOH (3.5 mL). After 20 h, $NaHCO_3$ (110 mg) was added and the mixture diluted with diethyl ether (20 mL). The mixture was dried ($MgSO_4$), filtered, evaporated, and purified by flash column chromatography on silica gel (60% EtOAc/hexanes→67%→75%) which gave 15 3-[4-Fluoro-2-((1R,2R,3R,4R)-3-hydroxymethyl-7-oxa-bicyclo[2.2.1]hept-2-ylmethyl)-phenyl]-propionic acid methyl ester (339 mg, 1.05 mmol, 88% from the ester of Example 14).

EXAMPLE 16

(1R, 2S, 3R, 4R)-3-[5-fluoro-2-(2-methoxycarbonyl-ethyl)-benzyl]phenyl)-7-oxa-bicyclo[2.2.1]heptane-2-carboxylic acid. A solution of the ester of Example 15 (336 mg, 1.04 mmol) in acetone (8 mL, B & J brand) was treated dropwise with Jones reagent (0.8 mL, 2.0 mmol, 2.5 M). The orange mixture was allowed to stir for 35 min. and then was quenched by addition of 0.5 mL isopropyl alcohol. After 15 min., the mixture was filtered through celite and evaporated. The residue was partitioned between 10 mL 1 M HCl and 20 mL $CH_2Cl_2$. The aqueous layer was extracted further with $CH_2Cl_2$ (2×20 mL) and the combined $CH_2Cl_2$ solution dried ($MgSO_4$), filtered and evaporated to give crude 16 (338 mg, 1.00 mmol, 97%).

EXAMPLE 17

(S)-2[(1-{(1R, 2S, 3R, 4R)-3-5-fluoro-2-(2-methoxycarbonyl-ethyl)-benzyl]-7-oxa-bicyclo[2.2.1]hept-2-yl}-methanoyl]-amino]-3-hydroxy-propionic acid benzyl ester.

The crude acid 16 (338 mg, 1.00 mmol, ) was co-evaporated with benzene and the residue was taken into dry THF (4.3 mL, Aldrich). The solution was cooled in an ice bath and 1-hydroxybenzotriazole monohydrate (188 mg, 1.39 mmol, Aldrich), L-serine benzyl ester hydrochloride (259 mg, 1.12 mmol, Sigma), and triethylamine (0.31 mL, 2.22 mmol, Aldrich) were added. The mixture was stirred for 5 min. and then DCC (233 mg, 1.13 mmol, Aldrich) was added, rinsing the sides of the flask with 0.5 mL of THF. The mixture was allowed to slowly warm to room temperature.

After 18 h, the mixture was cooled in an ice bath and ethyl acetate (4.3 mL) was added. The resulting mixture was filtered, evaporated and purified by flash column chromatography on silica gel (100% ethyl acetate) which gave slightly impure product (475 mg). Recrystallization (hexanes/ethyl acetate) gave the pure amide of Example 17 (176 mg, 0.34 mmol, 34%).

EXAMPLE 18

(S)-2-{(1R, 2S, 3R, 4R)-3-[5-2-(2-methoxycarbonyl-ethyl)-benzyl]-7-oxa-bicyclo[2.2.1]hept-2-yl{-4,5-dihydro-oxazole-4-carboxylic acid benzyl ester. $PPh_3$ (120 mg, 0.46 mmol, Aldrich) and i-$Pr_2$NEt (82 µL, 0.47 mmol, Aldrich) were added to a solution of the amide of Example 17 (153 mg, 0.30 mmol) in dry $CH_2Cl_2$ (0.26 mL, Aldrich) and dry $CH_3CN$ (1.0 mL, Aldrich). $CCl_4$ (43 µL, 0.45 mmol, Aldrich) was added dropwise and after 4 h of stirring, the solution was cooled in an ice bath and ethyl acetate (3 mL) and saturated aqueous $NaHCO_3$ solution (1 mL) were added. The mixture was poured into saturated aqueous NaCl solution (10 mL) and was extracted with ethyl acetate (10 mL). The organic portion was washed with saturated aqueous NaCl solution (10 mL) and then was dried ($MgSO_4$), filtered, evaporated and purified by flash column chromatography on silica gel (2:1 EtOAc/hexanes) to give the oxazoline of Example 18 (102 mg, 0.21 mmol, 69%).

EXAMPLE 19

2-{(1R, 2S, 3R, 4R)-3-[5-fluoro-2-(2-methoxycarbonyl-ethyl)-benzyl]-7-oxa-bicyclo[2.2.1]hept-2-yl}-oxazole-4-carboxylic acid benzyl ester. The oxazoline of Example 18 was co-evaporated with benzene and then taken into dry $CH_2Cl_2$ (1 mL, Aldrich). The solution was cooled in an ice bath and DBU (30 µL, 0.20 mmol, Aldrich) and $BrCCl_3$ (19 µL, 0.19 mmol, Aldrich) were added. The solution was allowed to stand at 0° C. for 17 h and then was diluted with $CH_2Cl_2$ (10 mL). The $CH_2Cl_2$ solution was washed with saturated aqueous $NH_4Cl$ solution (2×5 mL) and the combined aqueous solution extracted with EtOAc (2×10 mL). The combined organic solution was dried ($MgSO_4$), filtered, evaporated, and purified by flash column chromatography on silica gel (40% ethyl acetate/hexanes) to give the oxazole of Example 19 (74 mg, 0.15 mmol, 75%).

EXAMPLE 20

2-{(1R, 2S, 3R, 4R)-3-[5-fluoro-2-(2-methoxycarbonyl-ethyl)-benzyl]-7-oxa-bicyclo[2.2.1]hept-2-yl}-oxazole-4-carboxylic acid. $Pd(OH)_2$/C (17 mg, 20%, Aldrich) was added to a solution of the oxazole of Example 19 (74 mg, 0.15 mmol) in ethyl acetate (1.4 mL, B & J brand). The mixture was stirred under a balloon of $H_{2(g)}$ for 2 h and then was filtered through celite. Evaporation of the ethyl acetate left the acid of Example 20 (63 mg, 0.16 mmol, 100%) as a white crystalline solid.

EXAMPLE 21

3-(2-{(1R, 2R, 3S, 4R)-3-[4-(4-Cyclohexyl-butylcarbamoyl)-oxazol-2-yl]-7-oxa-bicyclo[2.2.1]hept-2-ylmethyl)-4-fluoro-phenyl)-propionic acid methyl ester. The acid of Example 20 (26 mg, 0.064 mmol) was co-evaporated with benzene and the residue taken into dry $CH_2Cl_2$ (0.3 mL, Aldrich). Dry DMF (small drop, Aldrich) was added followed by $(COCl)_2$ (11 µL, 0.13 mmol, Aldrich) which caused immediate gas evolution. After 30 min., the volatiles were removed and the residue co-evaporated twice with toluene to leave an off-white solid.

The crude acid chloride was taken into dry $CH_2Cl_2$ (0.36 mL, Aldrich) and $Et_3N$ (21 µL, 0.15 mmol, Aldrich) was added. 4-cyclohexylbutylammonium chloride (18 mg, 0.094 mmol) was then added and the reaction stirred for 1.5 h. The mixture was partitioned between 10 mL EtOAc and 10 mL 1 M HCl. The aqueous layer was extracted with 10 mL EtOAc and the combined EtOAc solution dried ($MgSO_4$), filtered, evaporated, and purified by flash column chromatography on silica gel (50% EtOAc/hexanes) to give the ester of Example 21 (27 mg, 0.05 mmol, 78%) as a white solid.

EXAMPLE 22

3-(2-{(1R, 2R, 3S, 4R)-3-[4-(4-Cyclohexyl-butylcarbamoyl)-oxazol-2-yl]-7-oxa-bicyclo[2.2.1]hept-2-ylmethyl}-4-fluoro-phenyl)-propionic acid. A solution of the ester of Example 21 (26 mg, 0.048 mmol) in THF (0.15 mL, Aldrich) and MeOH (0.75 mL, B & J Brand) was treated with 1 M NaOH solution (0.29 mL, 0.29 mmol). After 17 h, The solution was partitioned between 10 mL $CH_2Cl_2$ and 10 mL 1 M HCl. The aqueous layer was extracted with $CH_2Cl_2$ (2×10 mL) and the combined $CH_2Cl_2$ solution dried ($MgSO_4$), filtered, evaporated, and purified by flash column chromatography on silica gel (5% MeOH/$CH_2Cl_2$) to give the oxazole of Example 22 (24 mg, 0.046 mmol, 95%) as a white solid.

500 MHz $^1$H NMR (CDCl$_3$, ppm) δ 8.13 (s, 1 H) 7.11-7.08 (m, 2 H) 6.85-6.80 (m, 2 H) 4.97 (d, J=4.4 Hz, 1 H) 4.37 (d, J=4.8 Hz, 1 H) 3.4-3.3 (m, 3 H) 2.84 (t, J=7.7 Hz, 2 H) 2.6-2.5 (overlapping m, 3 H) 2.35 (dd, J=14.5, 11.2 Hz, 1 H) 2.20 (dd, J=14.5, 4.9 Hz, 1 H) 1.9-1.1 (overlapping m, 20 H) 0.9-0.8 (m, 2 H). MS (EI) m/z 526.2831 (526.2843 calculated for $C_{30}H_{39}FN_2O_5$; error=2 ppm).

EXAMPLE 23

Figure 4:
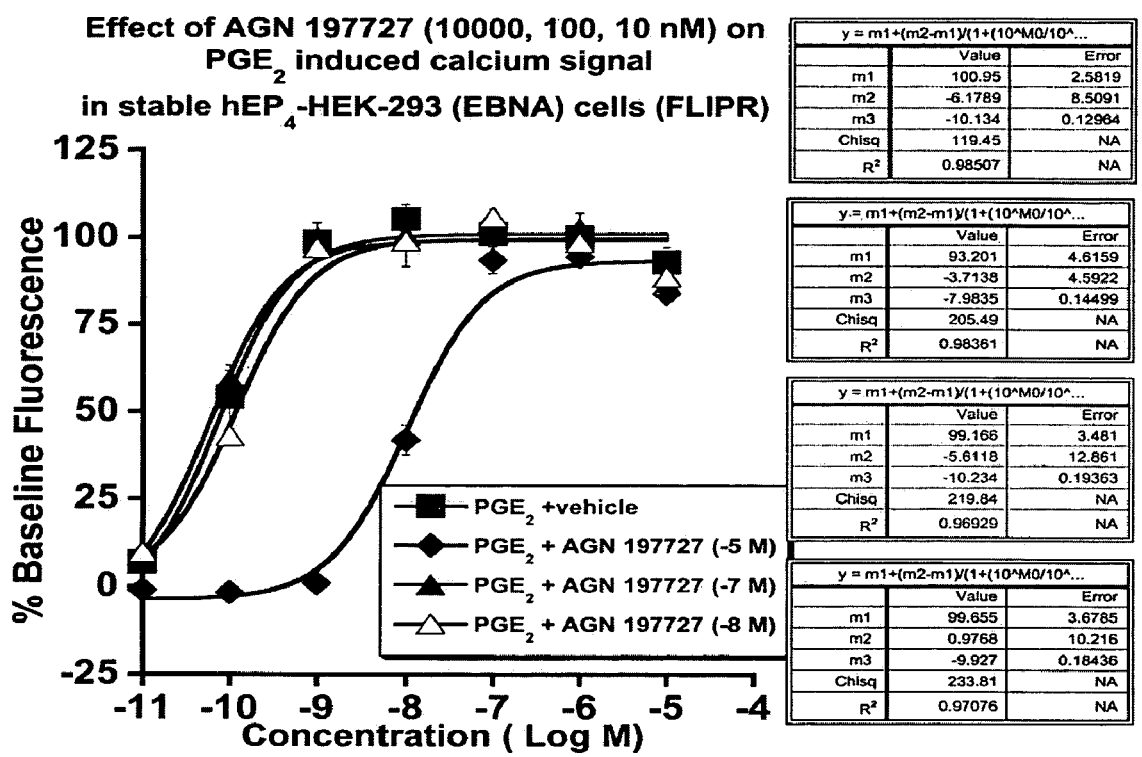
FIG. 4 shows the effect of compound 1 ($10^{-5}$ M, $10^{-7}$ M, and $10^{-8}$ M) on the activity of $PGE_2$, a known prostaglandin $EP_4$ agonist, on the induced calcium signal in stable HEK-293(EBNA) cells (FLIPR).
Figure 5:
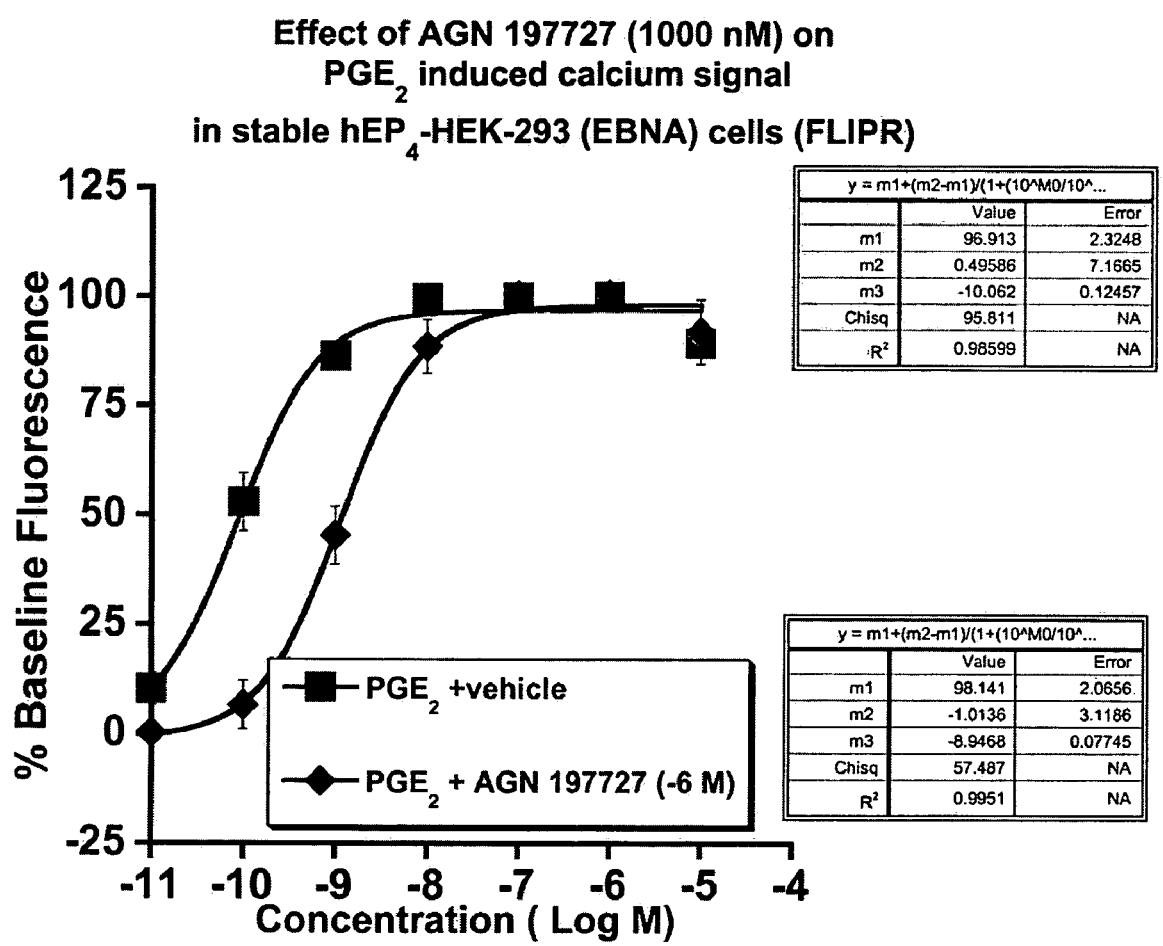
FIG. 5 shows the effect of compound 1 ($10^{-6}$ M) on the activity of $PGE_2$, a known prostaglandin $EP_4$ agonist, on the induced calcium signal in stable HEK-293(EBNA) cells (FLIPR).

Determination of the effect of compound 1 on the activity of Prostaglandin E2 on the induced calcium signal (FIG. 4): HEK-293(EBNA) cells, stably expressing cDNAs for the human EP$_4$ receptor and Gqs5 proteins, were seeded at a density of 5×10$^4$ cells per well in Biocoat® Poly-D-lysine-coated black-wall, clear-bottom 96-well plates (Becton-Dickinson) and allowed to attach overnight in an incubator at 37° C. Cells were then washed twice with HBSS-HEPES buffer (Hanks Balanced Salt Solution without bicarbonate and phenol red, 20 mM HEPES, pH 7.4) using a Denley Cellwash plate washer (Labsystems; Franklin, Mass.). After 45-60 min of dye-loading in the dark using the calcium-sensitive dye Fluo-4 AM, at a final concentration of 2 µM, plates were washed four times with HBSS-HEPES buffer to remove excess dye and leaving 100 µl buffer in each well. Plates were then placed into a FLIPR™ instrument and were allowed to equilibrate at 37° C. Drug solution was added in a 50 µl volume to each well to give the desired final concentration. Cells were excited with an Argon laser at 488 nm, and emission was measured through a 510-570 nm bandwidth emission filter (FLIPR™, Molecular Devices, Sunnyvale, Calif.). The peak increase in fluorescence intensity was recorded for each well. On each plate, the standard agonist PROSTAGLANDIN E2 was tested over a $10^{-11}$ to $10^{-5}$ molar concentration range in the presence of vehicle or test drug. Concentration-effect curves for Prostaglandin E2, as depicted in FIGS. 4-5, in the presence of vehicle and test drug were generated. FIG. 5 demonstrates the antagonistic activity of compound 1 at the human $EP_4$ receptor indicated by a dextral shift of the concentration-effect curve of PROSTAGLANDIN E2 in the presence of compound 1 (at $10^{-6}$ molar concentration) relative to vehicle control.

EXAMPLE 24

A nasal spray comprising compound 1 is administered to a patient 5 times per day until the symptoms subside.

EXAMPLE 25

A capsule comprising compound 1 is administered daily to a patient suffering from osteoporosis. Increase in bone density or reduction in bone density loss occurs for as long as the patient continues treatment.

EXAMPLE 26

A tablet comprising compound 1 is administered to a person suffering from a migraine headache. Significantly less pain is experienced by the patient.

EXAMPLE 27

A capsule or suppository comprising compound 1 is administered daily to a patient suffering from cancer. Improvement in the patient's condition occurs.

The present invention is not to be limited in scope by the exemplified embodiments, which are intended as illustrations of individual aspects of the invention. Indeed, various modifications of the invention in addition to those shown and described herein will become apparent to those skilled in the art from the foregoing description. Such modifications are intended to fall within the scope of appended claims.

What is claimed is:

1. A method of treating osteoporosis, colorectal cancer or migraine, comprising administering a therapeutically effective amount of a compound to a mammal in need thereof, wherein said compound has a formula

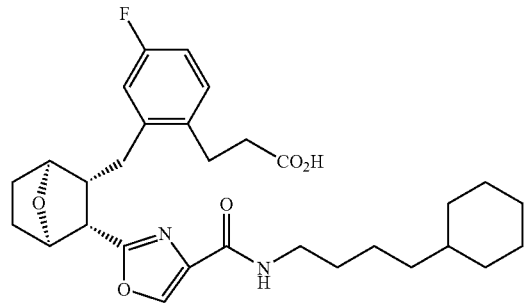

or is a pharmaceutically acceptable salt or a prodrug of a compound having the formula.

2. The method of claim 1, for treating osteoporosis.
3. The method of claim 1, for treating colorectal cancer.
4. The method of claim 1, for treating migraine.

* * * * *

UNITED STATES PATENT AND TRADEMARK OFFICE
CERTIFICATE OF CORRECTION

PATENT NO.        : 7,273,883 B2                                       Page 1 of 1
APPLICATION NO. : 10/952418
DATED             : September 25, 2007
INVENTOR(S)       : Woodward et al.

It is certified that error appears in the above-identified patent and that said Letters Patent is hereby corrected as shown below:

On The Title Page, Item (56), under "Other Publications", in column 2, line 14, delete "otent" and insert -- Potent --, therefor.

In column 1, lines 52–53, delete """ compounds" and insert -- "compounds --, therefor.

In column 2, line 5, delete "PGE2" and insert -- $PGE_2$ --, therefor.

In column 2, line 22, delete "insuffiency," and insert -- insufficiency, --, therefor.

In column 4, line 45, after "fibromyalgia" insert -- . --.

In column 4, line 61, after "granuloma" insert -- . --.

In column 4, line 63, after "scalds" insert -- . --.

In column 5, line 47, delete "distcarate" and insert -- distearate --, therefor.

In column 10, line 8, delete "5-fluro" and insert -- 5-fluoro --, therefor.

In column 14, line 12, in Claim 1, delete "migraine," and insert -- migraine --, therefor.

Signed and Sealed this

Eighteenth Day of December, 2007

JON W. DUDAS
*Director of the United States Patent and Trademark Office*